(12) United States Patent
Wilcox

(10) Patent No.: US 6,638,269 B2
(45) Date of Patent: Oct. 28, 2003

(54) CATHETER MOVEMENT CONTROL DEVICE AND METHOD

(76) Inventor: Robert L. Wilcox, 9213 NE. 151st St., Bothell, WA (US) 98011

( * ) Notice: Subject to any disclaimer, the term of this patent is extended or adjusted under 35 U.S.C. 154(b) by 0 days.

(21) Appl. No.: 10/131,874

(22) Filed: Apr. 25, 2002

(65) Prior Publication Data

US 2002/0133130 A1 Sep. 19, 2002

Related U.S. Application Data

(62) Division of application No. 09/810,680, filed on Mar. 19, 2001, now Pat. No. 6,391,010.

(51) Int. Cl.[7] .............................. A61M 5/00; B35D 1/04
(52) U.S. Cl. ......................... 604/528; 604/544; 215/6
(58) Field of Search .............................. 604/28, 36, 93, 604/181, 264, 275, 276, 327, 328, 500, 514, 517, 523, 528, 544; 251/6

(56) References Cited

U.S. PATENT DOCUMENTS

| | | | | |
|---|---|---|---|---|
| 3,135,259 A | * | 6/1964 | Evans | 604/412 |
| 4,850,573 A | * | 7/1989 | Simcock | 266/90 |
| 4,869,457 A | * | 9/1989 | Ewerlof | 251/6 |
| 4,919,389 A | * | 4/1990 | Hoekwater et al. | 251/6 |
| 5,147,341 A | * | 9/1992 | Starke et al. | 604/349 |
| 5,667,084 A | * | 9/1997 | Duggal et al. | 215/11.4 |
| 6,053,905 A | * | 4/2000 | Daignault et al. | 604/544 |
| 6,090,075 A | * | 7/2000 | House | 604/172 |
| 6,168,577 B1 | * | 1/2001 | Niederjohn et al. | 604/23 |
| 6,210,377 B1 | * | 4/2001 | Ouchi | 604/264 |
| 6,341,757 B1 | * | 1/2002 | Starchevich | 251/6 |
| 6,422,529 B1 | * | 7/2002 | Adelberg | 251/6 |
| 6,536,739 B1 | * | 3/2003 | Jensen | 251/6 |

FOREIGN PATENT DOCUMENTS

WO    WO 98/06642    *   2/2002    .......... B65D/83/10

* cited by examiner

*Primary Examiner*—Weilun Lo
*Assistant Examiner*—Michael G. Bogart

(57) ABSTRACT

A catheter movement control device is provided which allows forward, extending movement of the catheter tube contained within a flexible package to the exterior thereof as required during insertion. The method of use includes moving the catheter tube through the control device to exit the catheter package where it is inserted into the urethra. If resistance is encountered during insertion a stop member firmly engages the catheter tube to prevent rearward movement of the catheter tube under normal urging.

8 Claims, 4 Drawing Sheets

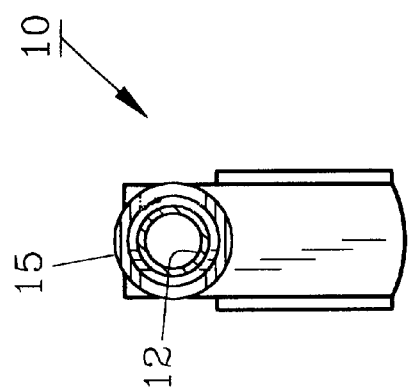
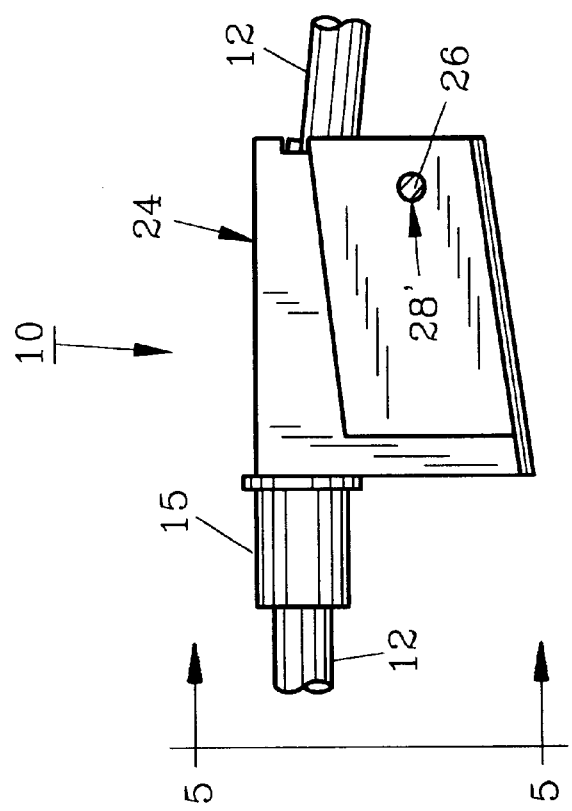
FIG. 5
FIG. 4

CATHETER MOVEMENT CONTROL DEVICE AND METHOD

This is a division of application Ser. No. 09/810,680 filed Mar. 19, 2001, now U.S. Pat. No. 6,391,010.

FIELD OF THE INVENTION

The invention herein pertains to catheters and in particular to urethral catheters which are packaged in a sterile environment for safe, easy and convenient use as the catheter tube is manipulated through an enclosed control device which remains within the package.

DESCRIPTION OF THE PRIOR ART AND OBJECTIVES OF THE INVENTION

Urethral and other catheters have long been manufactured in disposable, sterile, transparent polymeric packages for convenience. As such catheters have applied lubricants it is often difficult to control the insertion of the catheter tube which is formed from a lightweight, Inflexible, polymeric material, especially for those with relatively low hand grip strength. Insertion techniques vary and the personnel involved must be aware that an obstruction encountered in, for example, the urethral tract must be recognized and precautionary steps taken. Otherwise, forcing the catheter tube into or through an obstruction may cause severe or fatal injury to the patient. Accordingly, the catheter tube must be manually inserted in increments to the desired depth for proper fluid drainage. However, a slight resistance during insertion caused by a curve or narrowing in the urethral tract can be overcome or transgressed by slight additional insertion force. It is desirable to minimize or eliminate manual touching of the catheter tube once it is extended from the sterile interior of the package.

Conventional intravenous tubes are exterior to the body and sometimes utilize rollers to clamp or restrict the flow of fluids therethrough. Such clamping devices are generally open and expand since intravenous tubing is not inserted into the body and contamination of the clamp is of little concern. Contamination of a catheter tube can easily cause infections or the like to the patient and must be carefully avoided.

Thus, with the problems and difficulties associated with conventional catheters and catheter insertion techniques, the present invention was conceived and one of its objectives is to provide a device for controlling the catheter tube movement during the insertion process.

It is another objective of the present invention to provide a catheter control device which includes a stop member in the form of a roller to prevent rearward catheter movement.

It is also an another objective of the present invention to provide a catheter movement control device which will allow relatively inexperienced personnel or those with low grip strength to safely and conveniently insert a urethral catheter tube.

It is a further objective of the present invention to provide a method for controlling the movement and insertion of a catheter tube which allows the tube to be freely extended through a control device and from a slippery package, yet which will prevent rearward movement of the catheter tube, should a slight resistance during the extension process and insertion be realized.

Further objectives and advantages of the present invention will become apparent to those skilled in the art as a more detailed description is set forth below.

SUMMARY OF THE INVENTION

The aforesaid and other objectives are realized by providing a catheter movement control device which includes a generally closed housing with a catheter tube channel therein. A stop member is slidably positioned within the catheter housing proximate the tube channel. The interior side housing walls define channel grooves in which the stop member axles slide. The channel grooves are positioned so that the longitudinal axis of the catheter tube and the longitudinal axis of the stop member axle grooves intersect at an angle of approximately 35°. The control device is contained within a sealed, sterile catheter package with the tip of the catheter tube passing through a fitting on the exterior of the package. A cap seals the extending tip and maintains it in a sterile condition prior to use.

The method of use includes removing the cap and by manipulating the catheter tube through the control device contained within the package, the catheter tube is extended therefrom into the urethra. Should a slight resistance be encountered during extension, as occurs when a curve in the urethral tract is encountered, the catheter tube resists forward movement and additional manual force creates a rearward motion of the catheter tube. As the catheter tube initially moves in the rearward direction, the stop member moves into tight, frictional engagement with the catheter tube, and with additional forward force, the catheter tube transgresses such slight resistance caused by curves or the like in the urethral tract. However, should excessive rearward force be applied to the catheter tube, it will overcome or bypass the stop member and allow the catheter tube to move rearwardly into the package to thus prevent injury to the patient, for example, when an obstruction (as opposed to a slight narrowing) in the urethral tract exists.

BRIEF DESCRIPTION OF THE DRAWINGS

FIG. 4 features another view of the catheter movement control device of FIG. 3 in an enlarged side view;

FIG. 5 depicts the catheter control device as shown in FIG. 4 along lines 5—5 of FIG. 4;

DETAILED DESCRIPTION OF THE PREFERRED EMBODIMENTS AND OPERATION OF THE INVENTION

Figure 1:
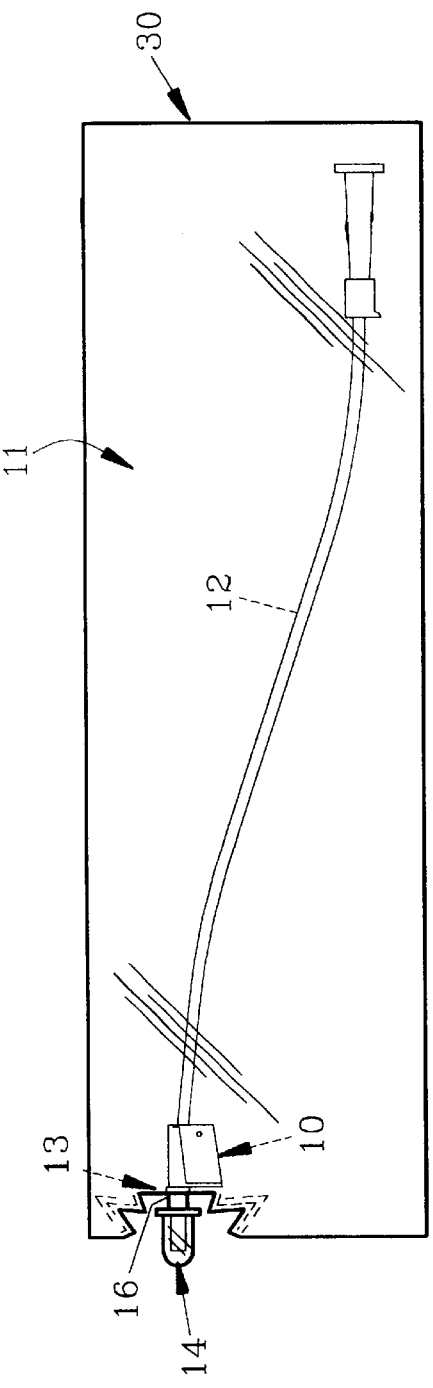
FIG. 1 demonstrates a conventional flexible catheter package containing the control device of the present invention.

For a better understanding of the invention and its operation, turning now to the drawings, FIG. 1 demonstrates preferred catheter movement control device 10 contained within a conventional sterile, sealed, transparent polymeric urethral catheter package 11. Catheter tube 12 within package 11 can be withdrawn therefrom through package opening 13 which tightly encloses fitting 15. Cap 14 is shown exteriorly of catheter package 11 which is removed before urethral catheter tube 12 is extended from package 11 and inserted in normal catheterization.

Figure 2:
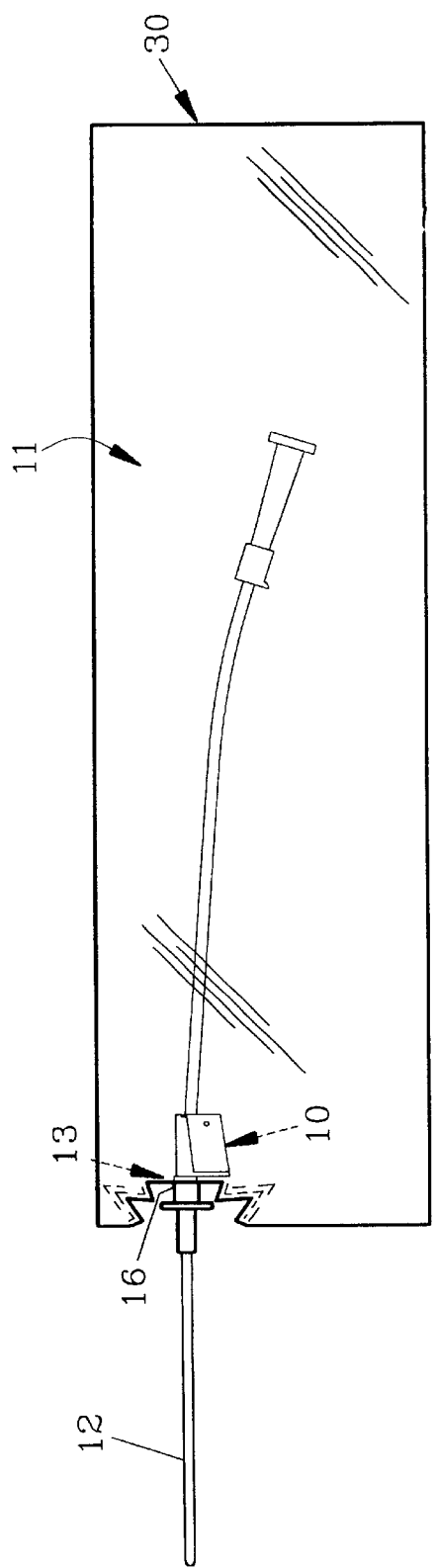
FIG. 2 illustrates the catheter package of FIG. 1 with the catheter tube in a somewhat extended posture.

In FIG. 2, catheter tube 12 is shown somewhat extended from catheter package 11 as manually manipulated during use. Catheter package 11 which is a two sided envelope may become a receptacle for drained urinary fluids or may be opened along its back end 30 and serve as a conduit for such drained fluids. As would be understood, catheter tube 12 is extended by exterior manual manipulation through control device 10 without hand contact of catheter tube 12 which passes through fitting 15 in opening 13, thus preserving the sterility of catheter tube 12 prior to urethral insertion.

Figure 3:
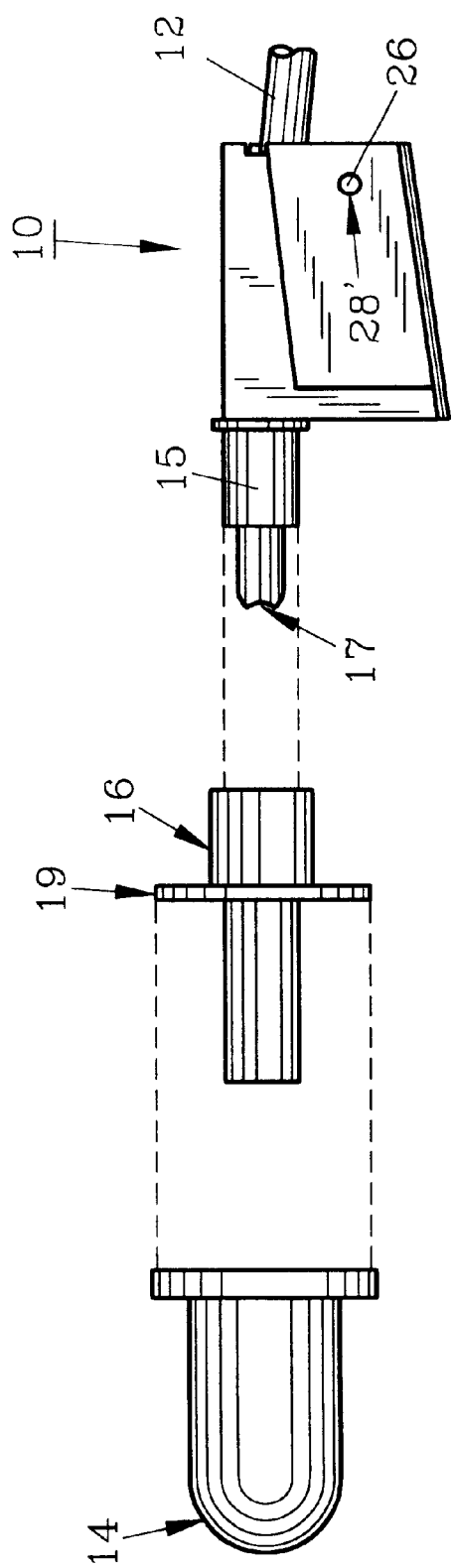
FIG. 3 shows an enlarged view of the catheter movement control device and other components as removed from the package.

As further shown in FIG. 3 fitting 15 is attached to preferred movement control device 10 and may be integrally formed therewith. Fitting 15 is sized to allow catheter tube 12 to slide therethrough. Fitting 15 extends through package opening 13 as shown in FIGS. 1 and 2 and exterior fitting 16 slides over fitting 15 with catheter package 11 positioned therebetween thereby sealing opening 13. Catheter tube 12 passes through fitting 16 and tip 17 of catheter tube 12 is then covered by cap 14 which is manually pressed onto sealing ring 19 for removal at the time of use. Catheter tube 12 is then enclosed and remains in a safe, sanitary condition prior to use. For clarity an enlarged side and front view of control device 10 is seen in FIGS. 4 and 5 with catheter tube 12 contained within fitting 15 and generally closed control device 10.

Figure 8:
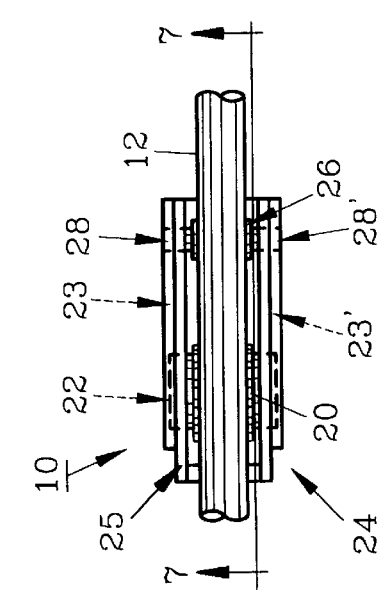
FIG. 8 illustrates a top view like that seen in FIG. 6 but with the stop member engaging the catheter tube.
Figure 9:
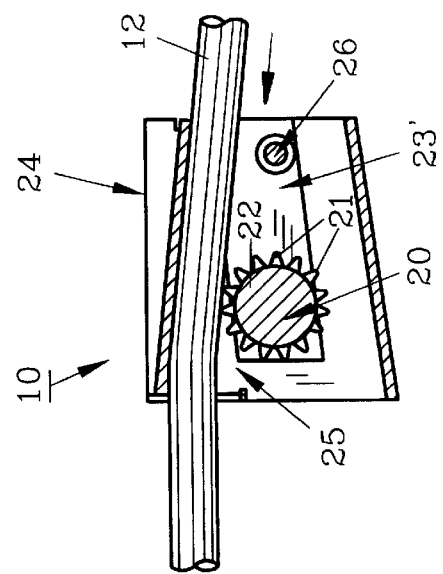
FIG. 9 demonstrates a side partial cross-sectional view of the control device with the stop member fully engaging the catheter tube to terminate rearward catheter tube movement as shown in FIG. 8 generally along lines 9–9.

As would be further understood, catheter tube 12 requires forward movement from package 11 through control device 10 for urethral insertion. However, such insertion is often difficult due to physical considerations, attitude and inexperience of-the particular personnel involved. As such, during the insertion procedure catheter tube 12 which is pre-lubricated may tend to withdraw, or not sufficiently penetrate the urethral tract as needed. To minimize such difficulties, control device 10 as shown in FIGS. 6–9 includes stop member 20 in the form of a roller having teeth 21 for engaging and gripping catheter tube 12 as shown in FIGS. 8 and 9. As seen in FIG. 7, catheter tube 12 is being extended through control device 10 and stop member 20 has moved in a forward (right to left) direction into contiguous engagement with catheter tube 12 as occurs when extending catheter tube 12 from package 11. In FIGS. 8 and 9, catheter tube 12 is being urged in a rearward direction (left to right) as may occur if urethral insertion terminates as by meeting resistance, causing stop member 20 to grip and deflect catheter tube 12 within catheter tube channel 25 of housing 24. From slight contact of stop member 20 and catheter tube 12 as shown in FIG. 7, additional rearward movement of catheter tube 12 drives stop member 20 rearwardly in a left to right direction to deflect and engage catheter tube 12 more severely, thereby terminating such rearward movement of catheter tube 12 relative to housing 24 as seen in FIGS. 8 and 9.

Also seen in FIGS. 7 and 9, stop member 20 includes axle 22 which is contained within housing side grooves 23, 23' of movement control device housing 24. Grooves 23, 23' are somewhat larger than the diameter of axle 22, thereby providing excess movement to stop member 20 as it turns and moves within housing 24. As further shown, due to the slanted nature of axle grooves 23, 23', stop member 20 frictionally engages or intersects catheter tube 12 within catheter tube channel 25 at an angle of approximately 35°. Housing 24 may be formed of a rigid, polymeric or other suitable materials as is stop member 20. Teeth 21 on stop member 20 help secure the grip as may be needed on a lubricated catheter tube.

Figure 6:
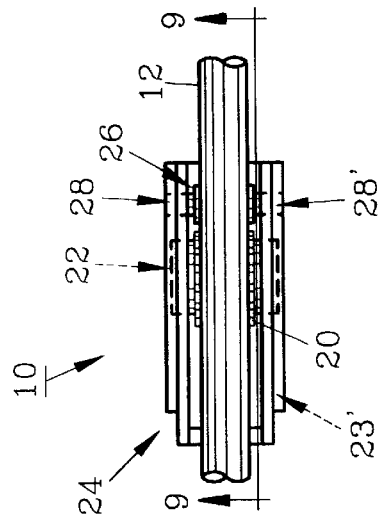
FIG. 6 pictures the catheter control device as shown in FIGS. 4 but with the top and fitting removed and with the stop member in initial contact.
Figure 7:
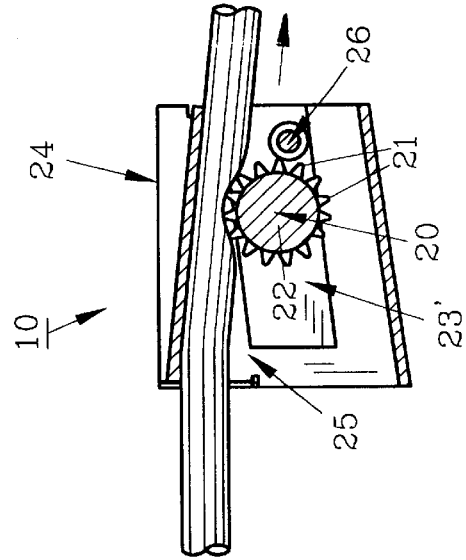
FIG. 7 provides a side partial cross-sectional view of the device as shown in FIG. 6 generally along lines 7–7 but with the top thereon.

Retaining roller 26 is mounted in housing side openings 28, 28' as seen in FIGS. 6 and 8 to prevent stop member 20 from escaping housing 24 as catheter 12 is urged in a rearward direction as demonstrated in FIG. 9. Stop member 20 thus moves rearwardly and stops when it contacts retaining roller 26, thus preventing stop member 20 from inadvertently exiting housing 24.

The preferred method of controlling the amount of movement of a catheter using control device 10 as contained within package 11 seen in FIGS. 1 and 2 includes the step of removing cap 14 from fitting 16 and manually urging catheter tube 12 forwardly through fitting 16. Next, catheter 12 is initially inserted into the urethra of the individual. Thereafter, catheter tube 12 within package 11 is carefully manually urged from outside of package 11 through control device 10, also in a forward direction to extend catheter tube 12 from package 11 and deeper into the urethra. Slight resistance incurred during the insertion process may cause catheter tube 12 to terminate its forward movement. Strong resistance may cause catheter tube 12 to move in a rearward direction. When this occurs, control device 10 allows stop member 20 to engage catheter tube 12 as seen in FIG. 9 thereby quickly terminating the rearward movement of catheter tube 12. Further forward urging of catheter 12 will allow catheter tube 12 to move rearwardly, past stop member 20, as in the case of a urethral blockage, thus preventing injury to the patient as catheter tube 12 slides rearwardly while engaged.

The illustrations and examples provided herein are for explanatory purposes and are not intended to limit the scope of the appended claims.

I claim:

1. A method of controlling the movement of a catheter having an extendable tube contained within a package with a control device having a stop member comprising a roller which will slide forwardly and rearwardly, said stop member mounted to engage the catheter tube, comprising the steps of:

a) urging the catheter tube through the control device in a forward direction to extend the catheter tube from the package; and b) engaging the catheter tube with the stop member by sliding the stop member within the control device to tightly engage the catheter tube to thereby prevent the catheter tube from withdrawing into the package.

2. The method of claim 1 whereby urging the catheter tube in a forward direction comprises the step of disengaging the stop member from the catheter tube.

3. The method of claim 1 whereby engaging the catheter tube further comprises the step of gripping the catheter tube with the outer surface of the roller.

4. The method of claim 1 whereby preventing the catheter tube from withdrawing comprises the step of deflecting the surface of the catheter tube with the roller to grip the same.

5. A method of controlling the movement of a catheter having an extendable tube contained within a package with a control device having a slidable stop member comprising a roller with radially extending teeth, said control device mounted so said roller teeth contact the catheter tube, comprising the steps of:

a) urging the catheter tube through the control device in a forward direction to extend the catheter tube from the package; and b) sliding the roller within the control device, and c) engaging the catheter tube with the teeth of the roller to thereby prevent the catheter tube from withdrawing into the package.

6. The method of claim 5 whereby urging the catheter tube in a forward direction comprises the step of slidably disengaging the roller from the catheter tube.

7. A method of controlling the movement of a catheter having an extendable tube contained within a package with a control device having a stop member comprising a slidable roller with radially extending teeth, said control device mounted on the catheter tube, comprising the steps of:

a) urging the catheter tube through the control device in a forward direction to extend the catheter tube from the package;

b) sliding the roller within the control device; and c) engaging the catheter tube with the teeth of the stop member roller to thereby prevent the catheter tube from moving in a rearward direction.

8. The method of claim 7 whereby urging the catheter tube in a forward direction comprises the step of disengaging the roller from the catheter tube.

* * * * *